United States Patent [19]
Leon

[11] Patent Number: 5,231,992
[45] Date of Patent: Aug. 3, 1993

[54] LOW-IMPACT CERVICAL CELL AND FLUID COLLECTOR

[76] Inventor: Arnaldo C. Leon, 707 Lavida, Arcadia, Calif. 91007

[21] Appl. No.: 805,301

[22] Filed: Dec. 10, 1991

Related U.S. Application Data

[63] Continuation-in-part of Ser. No. 532,818, Jun. 4, 1990, abandoned.

[51] Int. Cl.$^5$ ............................................. A61B 10/00
[52] U.S. Cl. ................................... 128/759; 128/769; 128/841; 604/330; 604/55
[58] Field of Search ............... 128/831, 832, 759, 769, 128/762, 749, 833–841, 757, 758; 604/1, 327–330, 55

[56] References Cited

U.S. PATENT DOCUMENTS

| | | | |
|---|---|---|---|
| 2,844,150 | 7/1958 | Draghi | 128/759 |
| 2,847,000 | 8/1958 | Nieburgs . | |
| 3,688,763 | 9/1972 | Cromarty | 128/759 |
| 3,850,160 | 11/1974 | Denson | 128/759 |
| 3,864,213 | 2/1975 | Bucalo | 128/769 |
| 4,311,543 | 1/1982 | Strickman | 128/833 |
| 4,628,941 | 12/1986 | Kosasky . | |

FOREIGN PATENT DOCUMENTS

| | | | |
|---|---|---|---|
| 87/01581 | 3/1987 | PCT Int'l Appl. | 604/330 |
| 1455107 | 11/1976 | United Kingdom . | |

*Primary Examiner*—Robert A. Hafer
*Attorney, Agent, or Firm*—Poms, Smith, Lande & Rose

[57] ABSTRACT

A cervical cell and fluid collector includes a substantially disc-shaped main body made of a high-density, non-absorbent, non-fibrous, biologically inert polyurethane foam. A porous membrane is mounted in a mainly concave collection recess in the main body. When the collector is in place adjacent to the cervix of a patient, cells and fluids adhere to the outer surface of the membrane. A layer of a cell-moistening material or agent is provided between the membrane and the inner surface of the recess; the cell-moistening material is preferably a pre-hydrated polymer gel that releases water during cell collection for moistening collected cells through the pores of the membrane when the cells are adhered to the outer surface of the membrane. The main body has an inward-slanting annular lip defining the recess and resiliently holding the membrane. The collector may remain in the vaginal cavity of the patient for up to at least 24 hours.

8 Claims, 1 Drawing Sheet

LOW-IMPACT CERVICAL CELL AND FLUID COLLECTOR

CROSS-REFERENCE TO RELATED APPLICATIONS

This is a continuation-in-part of U.S. patent application Ser. No. 07/532,818, filed on Jun. 4, 1990 now abandoned.

FIELD OF THE INVENTION

This invention relates to an intravaginal device for collecting cells and fluids from the uterus for use in diagnostic testing.

BACKGROUND OF THE INVENTION

Safe and efficient collection of cell and fluid samples from a woman's genital tract is crucial to early and accurate diagnosis of many diseases. The Papanicolaou Test (widely known as the "Pap Test") is, for example, commonly performed on women in order to test for cervical cancer. According to the Pap Test, cell samples are smeared onto a glass slide and are then examined after staining. The diagnosis of many other diseases also depends on efficient collection of cell and fluid samples from the cervical area.

There are accordingly several known devices for collecting cellular material from the vaginal tract. The U.K. Patent No. 1,455,107 (Denson, Nov. 10, 1976), for example, describes a diagnostic tampon for collecting samples from the female genital tract. The Denson tampon comprises a semi-rigid cylindrical supporting body that is at least partially covered with a removable film; in one embodiment, the film is porous. When the Denson tampon is used for a Pap Test, it is inserted into the vagina to the point of contact with the cervix. Cells in the cervical area attach themselves to the film jacket of the tampon. After only a matter of minutes, the tampon is removed and the cells collected on the film are smeared onto slides and stained as in the conventional Pap Test.

The greatest drawback of the Denson tampon is the very fact that it is a tampon. Not only would it be very uncomfortable to leave a tampon-like cell collector in the vaginal cavity of a patient for long periods, but it also increases the risk that the patient will suffer from toxic shock. Consequently, a tampon device is ill-suited for collecting cell and fluid samples over periods longer than a few minutes or hours. It would be preferable to be able to leave a cell collector in the vaginal cavity for a long as twenty-four hours in order to obtain cell and fluid samples over an entire daily cycle of the patient's body.

U.S. Pat. No. 2,847,000 (Nieburgs, Aug. 12, 1958), describes yet another diagnostic tampon. In the Nieburgs device, a tampon is secured to a plunger within a cardboard tube. The tube is inserted into the vaginal cavity of the patient and the tampon is then pushed by the plunger so that it extends outside of the tube and absorbs samples from the cervical area. Thereafter, the tampon is retracted within the tube and passes over a slide that is mounted inside the tube. The tube, in which the slide has been smeared with fluids and cells collected by the tampon, may then be placed in an ordinary mailing container and shipped to a laboratory for examination. Like other tampon devices, the Nieburgs collector is not designed for collecting cell samples over a periods longer than a few minutes. The size and operation of the Nieburgs device also increase the discomfort of the patient.

U.S. Pat. No. 4,628,941 (Kosasky, Dec. 16, 1986) describes a cervical mucus collector that uses an arrangement in which a plunger pushes a collecting tip within a tube against the cervix. The Kosasky device is intended primarily for the patient to use on herself. A cup is attached to the inner end of the insertion tube in order to guide the tip of the plunger against the cervix, and the cup has a slitted cover that prevents contact by the plunger tip with unwanted vaginal fluids.

Like other cervical sample collectors, the Kosasky device is neither designed nor suited for collecting samples over more than short periods. The information gained from the cells and fluids collected during short sample times is naturally less than if one were able to collect samples over a period of a full day or more. Furthermore, the tubes and plungers used in devices such as are described in the Denson, Nieburgs, and Kosasky patents all constitute additional medical waste that must be disposed of.

An additional disadvantage of existing cervical cell collectors is that it is necessary or at least preferable to produce smears very soon after the devices are used in the patient, since there is no way to keep the cells moist and viable during collection. Therefore, not only can existing devices not be left in the vaginal cavity long enough to collect cell samples during an entire daily cycle, but also the cells that they do collect can often dry out and provide much less diagnostic information than they could if they could be kept moist up until the time of examination.

It is accordingly an object of this invention to provide a device for collecting cells and fluids from the cervical area that is small enough, comfortable enough, yet efficient enough to obtain samples at least over a full 24-hour period with a much lower risk of irritation or shock caused by the presence of a foreign object in the vaginal cavity.

It is a further object of the invention to provide a cervical cell collector that keeps collected cells moist until the device is removed from the patient and can be examined quickly using conventional methods.

SUMMARY OF THE INVENTION

Accordingly, a collector according to the invention for collecting cells and fluids from the cervical area of a patient comprises a main body, a porous membrane, and a layer of a cell-moistening material or agent between the membrane and the main body. During collection, the membrane, which has an inner surface and an outer surface, is adjacent to the cervix of the patient whereby collected cells adhere to the outer surface. The layer of a cell-moistening material or agent is adjacent to the inner surface of the membrane for moistening cells through the pores of the membrane when the cells are adhered to the outer surface of the membrane.

In a preferred embodiment, the main body is substantially disc-shaped and includes a recess with an inner surface. In this embodiment, the membrane is substantially circular and is located within the recess outward from the layer of cell-moistening agent. Also in the preferred embodiment, the main body includes an inward-slanting annular lip that defines the mainly concave recess and resiliently holds the membrane.

The cell-moistening agent is preferably a prehydrated polymer gel. Also, the main body in the preferred embodiment is manufactured of high-density, non-absorbent, non-fibrous polyurethane, whereby the collector remains in the vaginal cavity of the patient for at least 24 hours.

DETAILED DESCRIPTION

Figure 1:
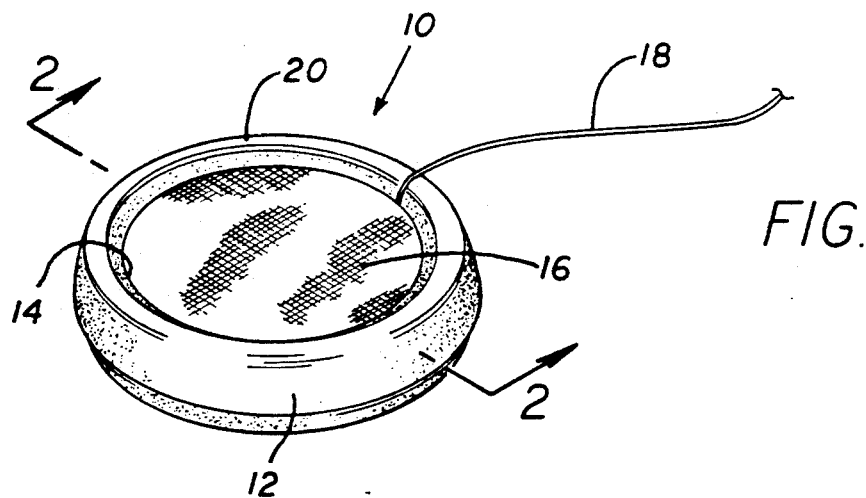
FIG. 1 is a perspective view of a device according to the invention for collecting cells and fluids from the cervical area of a patient.

Referring to FIG. 1, a cervical cell and fluid collector according to the invention is indicated generally by reference number 10. The collector 10 includes a preferably concave, substantially disk-shaped main body 12, preferably made from high density polyurethane. The main body 12 preferably includes a generally concave recess 14 into which a porous collection membrane 16 is mounted. The edges of the main body 12 are preferably smoothly rounded so as to minimize the discomfort to the patient when the collector is in the vaginal cavity.

A string, preferably of silk or of another biologically inert material, is preferably attached in a known manner to the main body 12 to enable the device to be removed easily from the vaginal cavity by pulling on the string 18. The string 18 makes it easier to remove the collector 10, but it is not necessary for the proper use of the collector according to the invention.

Figure 2:
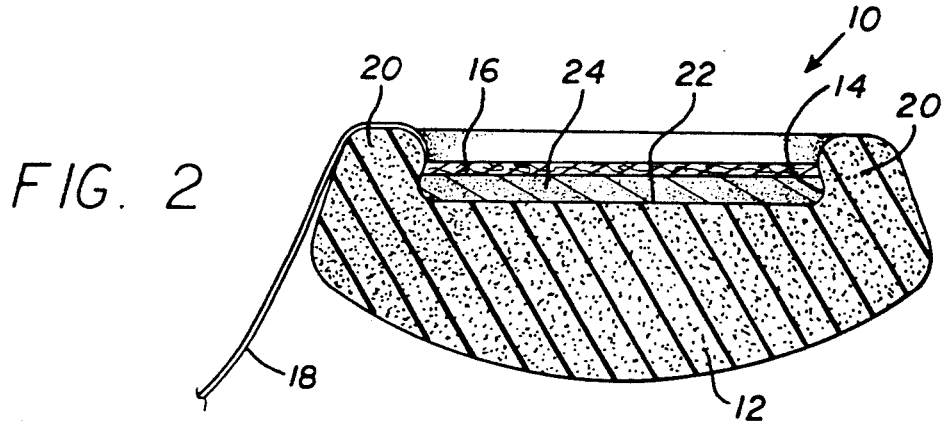
FIG. 2 is a cross-sectional view of the cervical cell and fluid collector according to the invention, taken along line 2—2 in FIG. 1.

As is seen in the cross-sectional view in FIG. 2, the main body 12 preferably has an annular lip 20 that curves slightly inward in order to form the generally concave recess 14. Within the recess 14 is a generally flat inner surface 22. The diameter of the membrane 16 is preferably greater than the smallest diameter of the recess 14 so that it can be mounted in the main body easily by fitting it within and under the inward-curving lip 20. The concave recess 14 fits well in the cervical area of the uterus. Furthermore, by making the main body 12 of a sponge-like foam material, the cervix or vaginal walls can grasp the sponge and hold it in place securely without undue discomfort.

By choosing the density of the main body 12 so that it is sufficiently firm (yet still resilient), the lip 20 will hold the membrane 16 securely when the collector is in the patient's genital tract. Alternatively, in order to reduce even further any chance that the membrane will slip out, the inner surface of the lip 20 may be provided with an annular groove into which the perimeter of the membrane fits when the membrane is mounted in the recess 14. The lip 20 may also extend farther over the membrane than is indicated in FIG. 2 in order to hold the membrane more securely, or to form a holding groove between the lip and the inner surface of the recess 14.

According to the invention, the collector 10 also includes a layer of a moistening or hydrating material or agent, preferably a water-releasing gel 24, between the membrane 16 and the inner surface 22 of the main body 12. The gel is preferably a polymer matrix that slowly releases water.

The U.S. manufacturer Replens manufactures such a carbophillic gel under the name Carbometer 934 P. Water is pre-stored in the gel during manufacturing and slowly leaches out of the polymer matrix when in use. Such gels are at present used, for example, to moisten the vaginal tract of elderly gynecological patients. The gel 24 is biologically inactive. Any biologically inert water-releasing gel may be used according to the invention in the gel layer 24.

Furthermore, it is also possible to use other synthetic and natural materials than the gel as the moistening material, as long as the material is biologically inert and can pre-store enough water and release it sufficiently slowly to moisten collected cells during the entire collection period. For example, a layer of open-cell foam with sufficiently small cells could be "packed" with water under pressure and a layer of this pre-hydrated foam could be used instead of the gel layer, especially when it is not necessary to collect cells for a full twenty-four hours.

The membrane 16 is porous, and is made preferably of a biologically inert synthetic material such as nitrocellulose or nylon. The membrane should not be so thick that it loses flexibility and risks breaking when inserted into a patient. A thickness on the order of 1 mm or less is preferred, although thicker membranes may be used if necessary precautions against breaking are taken.

When collecting cervical cells or fluids, the collector 10 is inserted into the vaginal cavity of the patient until the membrane is in contact with or is immediately adjacent to the cervix. Cells, fluids, mucoproteinaceous material, polysacharides, etc., thereby attach themselves biophysically to the surface of the membrane 16. It is believed that the cells attach themselves to the surface of the membrane as a result of differing electrical charges of the cells and membrane.

One should note that it is not the purpose of the main body to absorb cells through the pores. Collected cells are preferably not to pass through the membrane, but rather are to attach themselves to its outer surface. Consequently, the size of the pores in the membrane should be smaller than the expected size of the cells one wishes to collect. For most diseases for which the cell collectors according to the invention will be used, the typical cell size is 15–25$\mu$ in diameter. A preferred pore diameter is 5$\mu$, since this size is readily commercially available for nitrocellulose membranes.

Pore sizes smaller than 5$\mu$ may also be used according to the invention if one wishes to collect even smaller cells than those in the range given above. The anticipated range of pore sizes is from 1$\mu$ to 10$\mu$, with 4–6$\mu$ being the preferred range, and 5$\mu$ being the most preferred pore size.

When the collector is in place adjacent to the cervix and cells are attaching themselves to the membrane 16, the gel 24 will release water through the pores of the membrane 16. The water thus released from the gel 16 will penetrate to the outer surface of the membrane 16 and will thereby moisten the attached cells. Unlike existing devices, the collector according to the invention thus keeps collected cells moist during the entire sampling period. This in turn keeps the collected cells viable, which, as is well known, provides better test results during later examination, since the cells examined are less deteriorated than they would be if they were allowed to dry out. Furthermore, the useful collection time is increased, since cells collected early in the process are moistened and prevented from drying out by the time the process is completed.

The thickness of the gel layer 24 may be determined by experiment so as to provide adequate water release during the entire collection period, which, according to the invention, may be up to 24 hours or, in some cases, even longer. A layer thickness of up to 5 mm is possible, although the preferred thickness is between 0.5 and 2 mm.

Furthermore, it should note that using high-density polyurethane foam as the material of the main body 12, the main body will not absorb water from the gel layer 24 and thus reduce the possible period of use of the collector. Gels that release other moistening agents or liquids besides water may also be used, although water is the preferred moistening agent since it affects the collected cells the least.

An additional advantage of the polyurethane main body 12 is that it has the general structure of a sponge and is thus softer than the cotton which is often used in existing cervical cell collectors and tampon devices. Additionally, a sponge-like material such as polyurethane does not leave fragments or particles in the patient's genital tract after it has been removed, and it is deformable enough to fit comfortably in the patient without lessening its effectiveness.

The dimensions of the main body 12 are such that it can fit comfortably in the genital tract of the patient for as long as twenty-four hours or longer while being much less irritating than would a tampon device, especially such devices that require tube-like inserters or guide tubes. The outer diameter of the main body will normally be in the range from 40 mm to 52 mm, with a preferred diameter of from 43 to 47 mm, and a most preferred diameter of 45 mm.

The total thickness of the collector is approximately 15 mm, but may vary from 10 to 20 mm. Furthermore, as long as the main body 12 is sufficiently stiff to provide firm holding for the membrane and gel layer, the main body may be made even thinner than 10 mm. Also, although the collector 10 according to the invention may be made in different sizes for different groups of patients, the softness and deformability of the main body according to the invention make it possible to have a single collector whose size suits most patients.

Figure 3:
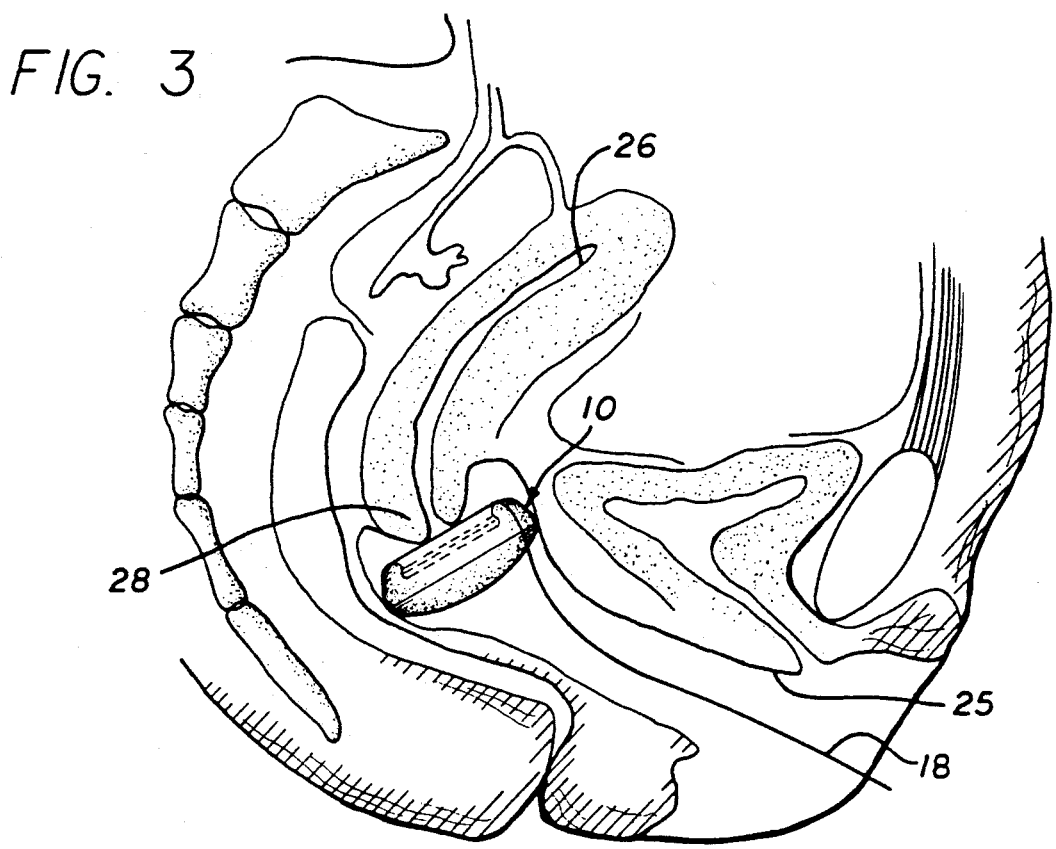
FIG. 3 illustrates the cell collector according to the invention in position adjacent to the cervix within the vaginal cavity of a patient.

FIG. 3 illustrates the location of the collector when in place in the patient's vaginal cavity 25. The uterus is indicated by reference number 26, and the cervix is indicated by reference number 28. As the figure shows, the string or cord 18 for removing the collector 10 preferably extends far enough so that it can be reached and pulled easily when it is time to remove the collector 10. In this respect, one should note that it is not necessary to attach the string 18 within the recess 14 as is indicated in FIG. 2, but rather the string may be attached using known methods at any secure and convenient location on the main body 12.

The collector 10 is preferably inserted manually into the patient. The examining physician can do this with her fingers while the patient is sitting, lying down, or even standing. There is no need for an applicator or inserter tube, although such applicators or inserters may be used as long as they do not damage the membrane or cause leakage of the gel layer 24 from under the membrane.

In the preferred test protocol, the collector is used for collection of cells and fluids from the uterus only during the intermenstrual period. The collector according to the invention may be used to test for cervical cancer, parasites, clamydia, trichomona, papiloma virus, herpes and AIDS (by collection of fluids), or for any other disease that manifests itself by the presence of cells or antibodies (which are proteins) that can attach themselves to the surface of the membrane 16.

The collector according to the invention may be used for rapid collection of cells, but in the preferred test protocol, the collector is left in place for about twenty-four hours in order to collect a full range of naturally desquamated cells and fluids from the exocervix, endocervix and uterus, and occasionally from the tubes and ovaries. Although the collector according to the invention may be left in place to collect cells for a full twenty-four hour period, it is of course not necessary to leave it in place that long if a shorter collection time would suffice for a particular test.

At the end of the test cycle, the patient should preferably return to the examining physician who will then remove the collector. The membrane 16 is then removed from the main body 12 of the collector 10 and is preferably fixed in alcohol, dried and otherwise prepared for laboratory testing, including staining according to the Papanicolaou staining techniques in the case in which the collector is being used to obtain cell samples for a Pap smear. Observe that it is not necessary to scrape collected cells from the surface of the membrane 16, although this is possible, since the membrane itself may be dissolved using known solvents without destroying the collected cells and fluids.

If the resiliency of the lip 20 of the main body 12 is insufficient to hold the membrane securely, adhesives or other mechanical means may be used to attach the membrane within the recess 14, provided that the material used is biologically inert, or is used in such small quantities that it cannot affect the test or irritate the patient.

Although the concave recess 14 improves the fit over the cervical area of the collector 10, it would also be possible to mount the membrane 16 flush with the upper surface (viewed as in FIG. 2) of the main body 12 with the gel layer 24 being located in a mainly cylindrical recess under the membrane. In such case, the membrane would be attached using adhesives or some mechanical attachment to the main body.

Although the main body is preferably disc-shaped, it could also be oval or oblong, in which case the membrane would be cut to fit in a corresponding recess.

Several alternatives to the preferred embodiment of the invention have been described above. All of these alternatives are encompassed by the following claims.

I claim:

1. A collector for collecting cells and fluids from the cervical area of a patient comprising:
   a substantially disc-shaped main body made of a high-density, non-absorbent, non-fibrous, biologically inert polyurethane foam that has a mainly concave collection recess having an inner surface, whereby the width of the disc-shaped main body is greater than the thickness of the disc-shaped main body;
   said main body being positioned in a non-blocking configuration adjacent to the cervical opening of the patient;
   a single porous, substantially circular and planar membrane attached to the main body which, during collection, is adjacent to the cervix of the patient, and which has an inner surface and an outer surface, whereby collected cells adhere to the outer surface;

said main body including an inward-slanting annular lip defining the recess and resiliently holding the membrane;

gel means comprising a layer of a pre-hydrated gel located adjacent to the inner surface of the membrane and between the membrane and the inner surface of the recess for releasing water during collection of cells, and for moistening and preserving collected cells through the pores of the membrane when the cells are adhered to the outer surface of the membrane; and whereby the collector remains in the vaginal cavity of the patient for at least 24 hours.

2. A collector for collecting cells and fluids from the cervical area of a patient comprising:

a substantially disc-shaped main body, whereby the width of the disc-shaped main body is greater than the thickness of the disc-shaped main body;

a porous membrane attached to the main body which, during collection, is adjacent to the cervix of the patient, and which has an inner surface and an outer surface, whereby collected cells adhere to the outer surface; and gel means comprising a pre-hydrated gel located adjacent to the inner surface of the membrane for releasing water through the pores of the membrane during collection of cells and for moistening and preserving collected cells when the cells are adhered to the outer surface of the membrane.

3. A collector as defined in claim 2, in which:

the main body includes a recess with an inner surface;

the gel means is adjacent to the inner surface of the recess; and the membrane is substantially circular and is located within the recess outward from the gel means.

4. A collector as defined in claim 3, in which the recess is substantially concave.

5. A collector as defined in claim 3, in which the main body includes an inward-slanting annular lip defining the mainly concave recess and resiliently holding the membrane.

6. A device as defined in claim 2, in which the main body is manufactured of high-density, non-absorbent, non-fibrous polyurethane, whereby the collector remains in the vaginal cavity of the patient for at least 24 hours to collect sample cells and fluids over an entire daily bodily cycle without significant cell deterioration.

7. A collector as defined in claim 2, in which the main body is positioned in a non-blocking configuration adjacent to the cervical opening of the patient.

8. A collector as defined in claim 2, in which the porous membrane is substantially planar and is removable from the main body.

* * * * *